United States Patent
Kim et al.

(10) Patent No.: US 9,644,956 B2
(45) Date of Patent: May 9, 2017

(54) METHOD AND APPARATUS FOR MEASURING THIN FILM THICKNESS USING X-RAY

(71) Applicant: NANO CMS Co., Ltd., Cheonan-si (KR)

(72) Inventors: Shi Surk Kim, Asan-si (KR); Joo Hye Kim, Suncheon-si (KR); Sang Bong Lee, Daejeon (KR); Seong Uk Lee, Cheonan-si (KR)

(73) Assignee: Nano CMS Co., LTD (KR)

( * ) Notice: Subject to any disclaimer, the term of this patent is extended or adjusted under 35 U.S.C. 154(b) by 573 days.

(21) Appl. No.: 13/893,395

(22) Filed: May 14, 2013

(65) Prior Publication Data

US 2014/0119513 A1 May 1, 2014

(30) Foreign Application Priority Data

Oct. 26, 2012 (KR) ........................ 10-2012-0119379

(51) Int. Cl.
*G01N 23/20* (2006.01)
*G01N 23/223* (2006.01)
*G01B 15/02* (2006.01)

(52) U.S. Cl.
CPC ....... *G01B 15/02* (2013.01); *G01N 23/20066* (2013.01); *G01N 23/223* (2013.01); *G01N 2223/063* (2013.01)

(58) Field of Classification Search
CPC ............... G01N 23/20; G01N 23/223; G01N 23/20066; G01N 2223/063; G01B 15/02
See application file for complete search history.

(56) References Cited

U.S. PATENT DOCUMENTS

| | | | |
|---|---|---|---|
| 5,195,117 A * | 3/1993 | Ong | 378/89 |
| 6,111,929 A * | 8/2000 | Hazlett | 378/45 |
| 6,399,944 B1 * | 6/2002 | Vasilyev et al. | 250/310 |
| 2002/0093648 A1 * | 7/2002 | Nikoonahad et al. | 356/237.1 |

FOREIGN PATENT DOCUMENTS

| | | |
|---|---|---|
| JP | 52125352 | 10/1977 |
| JP | 63085309 | 4/1988 |
| JP | 64041510 | 2/1989 |
| JP | 08334481 | 12/1996 |
| JP | 2010014432 | 1/2010 |

OTHER PUBLICATIONS

English Abstract of Published Japanese Patent Application No. 08-334481 Dec. 17, 1996.
English Abstract of Published Japanese Patent Application No. 52-125352 Oct. 21, 1977.

(Continued)

*Primary Examiner* — Glen Kao (57) ABSTRACT

Provided is an apparatus and method for measuring a thickness of thin film using x-ray where a thickness of a thin film of nanometer_(nm) level can be accurately measured without destructing an target sample, through determination of thickness of thin film of the target sample, by determining a calibration curve by comparing a difference of intensities of signals scattered by a special component included in a base layer of the reference sample.

15 Claims, 10 Drawing Sheets

(56) References Cited

OTHER PUBLICATIONS

English Abstract of Published Japanese Patent Application No. 63-085309 Apr. 16, 1988.
English Abstract of Published Japanese Patent Application No. 64-041810 Feb. 14, 1989.
English Abstract of Published Japanese Patent Application No. 2010-014432 Jan. 21, 2010.
Japanese Office Action for foreign counterpart of U.S. Appl. No. 13/893,395 Apr. 25, 2016.

* cited by examiner

METHOD AND APPARATUS FOR MEASURING THIN FILM THICKNESS USING X-RAY

Pursuant to 35 U.S.C. §119 (a), this application claims the benefit of an earlier filing date and right of priority to Korean Patent Application No. 10-2011-0119379, filed on Oct. 12, 2012, the contents of which is hereby incorporated by reference in its entirety.

BACKGROUND OF THE DISCLOSURE

Field of Endeavor

The present disclosure relates to a method for measuring a thickness of thin film using x-ray and an apparatus using the same, and more particularly to a method for measuring thickness of thin film layer using x-ray configured to use a special component included in base layer and/or thin film layer of a reference sample and a target sample and an apparatus thereof, and more further particularly to a method for measuring a thin nanometer-level film thickness using x-ray without destructing a target sample, and an apparatus using the method.

Background

This section provides background information related to the present disclosure which is not necessarily prior art.

The thin film thickness is conventionally measured by individually using an SEM (Scanning Electron Microscope), an FESEM (Field Emission Scanning Electron Microscope), an STEM (Scanning Transmission Electron Microscope), an eddy current sensing method, an ultrasonic method and a high energy sensitive method using X-ray, or in combination with each other. Among these methods, the X-ray using method is such that X-ray is irradiated to a target object such as film or thin film formed with a metal thin film and/or polymer to measure thickness using non-contact method in response to intensity of a signal obtained therefrom. The thin film thickness measuring method using X-ray may use a single object as a target or an object under production as a target.

For example, a thickness of a target object such as a metal thin film or a film can be measured in real time while the target object with a predetermined thickness is being manufactured by rolling method, one of the methods of manufacturing the target object, and a good quality of products can be manufactured with a constant even thickness by adjusting the thickness of the target object.

The non-contact thickness measuring device using X-ray may be such that an amount of quantum X-rays penetrating a target object is detected by a detector, or an amount of fluorescent X-rays penetrating a target object is detected to measure the thickness of the target object. The amount of quantum X-rays or the amount of fluorescent X-rays detected by the detector is changed by absorption coefficient, density and thickness in response to material of the target object, where an amount of quantum X-rays irradiated to and emitted from an X-ray target without a target object and an amount of X-rays irradiated to through a target object and emitted from the X-ray target through the target object are relatively compared, whereby a thickness of the target object can be learned by checking a relative difference therebetween.

However, the method of measuring a thickness of a target object by a difference of quantum amount emitted when a target is present and when a target object is absent using the X-ray suffers from disadvantages in that a basic premise is required of learning a difference of amount of quantum when a target object is absent such that it is difficult to apply this method to measurement of thickness alone formed on a substrate or a base layer, or to continuous process. Particularly, even if a sensitive X-ray method is used to a high energy, and if a thin film thickness is under several nanometers (nm), it is difficult to measure the thin film thickness of nanometer level.

Thus, there is a need to address the abovementioned disadvantages.

SUMMARY OF THE DISCLOSURE

This section provides a general summary of the disclosure, and is not a comprehensive disclosure of its full scope or all of its features.

Thus, there is a need for a thin film thickness measuring apparatus in a simple structure and a thin film thickness measuring method which can be used for thin film thickness of several nanometers, and therefore, it is an object of the present disclosure to accurately measure thin film thickness of several nanometers without destructing a target sample.

Furthermore, the present disclosure is to provide a method for measuring a thin film thickness configured to simply and easily measure only a thickness of a thin film by directly using as an object a target object having a thin film layer formed on a substrate or a base layer and to be usable for a unit process and a continuous process as well, and an apparatus thereof.

It should be emphasized, however, that the present disclosure is not limited to a particular disclosure, as explained above. It should be understood that other technical subjects not mentioned herein may be appreciated by those skilled in the art.

In one general aspect of the present disclosure, there is provided a method for measuring thickness of thin film using an x-ray, the method comprising:

detecting an intensity of a signal scattered by a special component included in a base layer by irradiating x-ray to the base layer of a reference sample;

detecting an intensity of a signal scattered by the special component included in the base layer by irradiating x-ray to a thin film layer formed on the base layer of the reference sample;

determining a calibration curve by comparing a difference between intensities of signals respectively detected from the base layer irradiation step and the thin film layer irradiation step with a thickness of the thin film layer;

detecting an intensity of a signal scattered by the special component included in a base layer by irradiating x-ray to a thin film layer formed on the base layer of a target sample; and determining the thickness of thin film layer of the target sample by comparing the difference between intensities of signals respectively detected from the base layer irradiation step and the target sample irradiation step with the calibration curve.

Preferably, but not necessarily, the base layer may be a glass substrate.

Preferably, but not necessarily, the thin film layer may be a thickness in the scope of 10~400 nm, and may be a metal layer selected from a group consisting of silver, copper, nickel, manganese, chrome, iron and gold.

Preferably, but not necessarily, the special component may be selected from a group consisting of C, H, O, Ca, Na, Si and Ag.

Preferably, but not necessarily, the special component may not be present in a thin film layer and but may be present only in the base layer.

Preferably, but not necessarily, the x-ray may be irradiated by a portable XRF (X-ray Fluorescence) spectrometer.

Preferably, but not necessarily, the method may further comprise measuring the thickness of thin film formed on the base layer of the reference sample using an electron microscope.

Preferably, but not necessarily, the calibration curve may be determined by the following Equation:

$$I/Io = \exp[-(\mu/\rho)X]$$ Equation 1

I: intensity of returning signal relative to thin film layer
Io: intensity of returning signal relative to base layer
$\mu$: attenuation coefficient of thin film layer
$\rho$: density of thin film layer
X: thickness of thin film layer Preferably, but not necessarily, the step of determining the calibration curve may include correction by comparing the difference between intensities of signals with the thickness of thin film layer.

In another general aspect of the present disclosure, there is provided an apparatus for measuring thickness of thin film using x-ray, the apparatus comprising:

an x-ray generator irradiating x-ray to a reference sample, a base layer of a target sample or a thin film layer of the target sample;

a detector detecting intensity of a signal scattered from the reference sample or the target sample; and a controller determining a calibration curve by comparing a difference of intensities of signals scattered by a special component included in a base layer of the reference sample having the base layer and having the base layer formed with the thin film layer with a thickness of the thin film layer, and determining the thickness of thin film layer of the target sample by comparing a difference of intensities of signals scattered by the special component included in the base layer of the target sample having the base layer formed with the thin film layer with the reference sample having the base layer with the calibration curve.

The apparatus and method for measuring for measuring a thickness of thin film using x-ray according to exemplary embodiments of the present disclosure have an advantageous effect in that a thickness of a thin film of nanometer-level can be accurately measured without destructing an target sample, through determination of thickness of thin film of the target sample, by determining a calibration curve by comparing a difference of intensities of signals scattered by a special component included in a base layer of the reference sample having a base layer and a base layer formed with the thin film layer with a thickness of the thin film layer, and determining the thickness of thin film layer of the target sample by comparing a difference of intensities of signals scattered by the special component included in the base layer of the target sample having the base layer formed with the thin film layer with the reference sample having the base layer with the calibration curve.

BRIEF DESCRIPTION OF THE DRAWINGS

In order to explain the principle of the present disclosure, some accompanying drawings related to its preferred embodiments are below reported for the purpose of illustration, exemplification and description, although they are not intended to be exhaustive. The drawing figures depict one or more exemplary embodiments in accord with the present concepts, by way of example only, not by way of limitations. In the figures, like reference numerals refer to the same or similar elements.

Thus, a wide variety of potential practical and useful embodiments will be more readily understood through the following detailed description of certain exemplary embodiments, with reference to the accompanying exemplary drawings in which.

DETAILED DESCRIPTION

The disclosed embodiments and advantages thereof are best understood by referring to FIGS. 1-19 of the drawings, like numerals being used for like and corresponding parts of the various drawings. Other features and advantages of the disclosed embodiments will be or will become apparent to one of ordinary skill in the art upon examination of the following figures and detailed description. It is intended that all such additional features and advantages be included within the scope of the disclosed embodiments, and protected by the accompanying drawings. Further, the illustrated figures are only exemplary and not intended to assert or imply any limitation with regard to the environment, architecture, or process in which different embodiments may be implemented. Accordingly, the described aspect is intended to embrace all such alterations, modifications, and variations that fall within the scope and novel idea of the present invention.

Meanwhile, the terminology used herein is for the purpose of describing particular implementations only and is not intended to be limiting of the present disclosure. The terms "first," "second," and the like, herein do not denote any order, quantity, or importance, but rather are used to distinguish one element from another. For example, a second constituent element may be denoted as a first constituent element without departing from the scope and spirit of the present disclosure, and similarly, a first constituent element may be denoted as a second constituent element.

As used herein, the terms "a" and "an" herein do not denote a limitation of quantity, but rather denote the presence of at least one of the referenced item. That is, as used herein, the singular forms "a", "an" and "the" are intended to include the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Also, "exemplary" is merely meant to mean an example, rather than the best. If is also to be appreciated that features, layers and/or elements depicted herein are illustrated with particular dimensions and/or orientations relative to one another for purposes of simplicity and ease of understanding, and that the actual dimensions and/or orientations may differ substantially from that illustrated.

That is, in the drawings, the size and relative sizes of layers, regions and/or other elements may be exaggerated or reduced for clarity. Like numbers refer to like elements throughout and explanations that duplicate one another will be omitted. As may be used herein, the terms "substantially" and "approximately" provide an industry-accepted tolerance for its corresponding term and/or relativity between items.

For reference, a thin film thickness and a thickness of thin film may be interchangeably used in the present disclosure.

Hereinafter, a method for measuring a thickness of thin film using x-ray and an apparatus using the same according to the present disclosure will be described in detail with reference to the accompanying drawings.

The method for measuring a thickness of thin film using x-ray is configured such that x-ray is respectively irradiated to a reference sample having a base layer formed with a thin film layer and to a target sample, and a thickness of the thin film of the target sample is measured using a difference of intensities of signal scattered by a special component contained in the base layer.

That is, a calibration curve is first determined by using a difference of intensities of signal scattered by a special component contained in the base layer changing in response to thickness of the thin film layer using as an object the reference sample having a base layer formed with a thin film layer, comparison is made with the calibration curve by determining an intensity of a signal scattered by the special component using as an object the target sample having a base layer formed with a thin film layer, and thickness of thin film layer is determined.

At this time, the thin film layer may be an organic thin film or an inorganic thin film, and may be preferably formed with a metal selected from a group consisting of silver, copper, nickel, manganese, chrome, iron and gold.

As results of checks by the present inventors, it was difficult to measure a thickness of a metal layer formed with titanium or molybdenum. Furthermore, the thin film layer was within a scope of 10~400 nm, preferably, within a scope of 50~300 nm, and it was difficult to measure the thickness using x-ray due to a calibration curve not being proportionally straight by electron emission coefficient if the thin film layer deviates from the scopes.

Furthermore, the base layer is a base formed with the thin film layer, and may be one of variable substrates known in the art or a layer stacked with one or more thin film layers. The present disclosure is characterized by using intensities of signals scattered by a special component contained in a base layer or other thin film layers existing under the thin film layer, where the base layer preferably includes one or more special components.

To this end, the present disclosure is sequentially performed by a base layer irradiation step, a thin film irradiation step, a calibration curve determining step, a target sample irradiation step and a thin film layer thickness determining step.

First, the base layer irradiation step is to irradiate x-ray to a base layer of a reference sample to detect an intensity of a signal scattered by a special component included in the base layer. That is, x-ray is irradiated to the base layer of the reference sample with no thin film layer to detect an intensity of signal, and the intensity of the signal is later compared with an intensity of a signal of a reference sample formed with a thin film layer to determine an intensity of signal changed (decreased) by the thin film layer.

The x-ray is irradiated to an organic thin film reference sample or an organic thin film target sample, where the x-ray may be generated from a target material of an x-ray generator or a radio isotope.

The x-ray irradiation step may include two methods, one being a method using an x-ray generator and the other being a method using a radio isotope.

The x-ray generator generates x-ray by allowing particles accelerated by photons and electrons to collide a target material inside the x-ray generator, as a step for generating a special x-ray, and emits only an intrinsic special x-ray for the target material when the generated x-ray passes a window of a device surface. As a result, the special x-ray generated from the target material inside the x-ray generator or the radio isotope is scattered by colliding with an organic thin film layer reference sample or an organic thin film target sample.

In the said process, the special x-ray generates an inelastic Compton scattering due to C, H and O elements existing in an organic thin film layer reference sample or an organic thin film target sample, which is an analytical material. For example, a base layer of a reference sample or a target sample formed with a glass substrate may include therein special components such as Ca and Na, and an intensity of a signal scattered by the special component may be detected by a portable X-ray Fluorescence (XRF) spectrometer.

The portable XRF spectrometer was conventionally used for measuring contents of special components contained in the thin film layer, but the present disclosure characteristically uses the XRF spectrometer for measuring a thickness of a thin film using an intensity of a signal in response to the special components. Hence, the special components according to the present disclosure may include any one material or more materials selected from a group consisting of C, H, O, Ca, Na, Si and Ag. However, the special component is preferably one component for accuracy sake, and the special component is more preferably present, not in a thin film layer, but in a base layer only.

The intensity of signal of scattered x-ray or inelastic Compton scattering line is changed by an incident angle ($\theta 1$) incident by the x-ray on the organic thin film layer reference sample or the organic thin film target sample and by an angle scattered therefrom (take-off angle, $\theta 2$), whereby an analytical performance such as detection limit can be enhanced by determination of an optimal angle in response to device conditions of the organic thin film layer reference sample or the organic thin film target sample.

The intensity of scattered signal may be detected by selection of Rayleigh elastic scattering x-ray generated after collision by a special x-ray with the organic thin film layer reference sample or the organic thin film target sample, or Compton inelastic scattering x-ray, or only Compton scattering signal in the fluorescence x-ray. The x-ray wavelength corresponding to the Compton scattering signal may be diffracted by using a solid-state crystal, and a special peak signal may be selectively detected by the Compton scattering using a detector arranged at a special angle. For analysis by using an area of peak in response to the Compton scattering, a goniometer may be mounted to detect a Compton scattering signal of a predetermined scope.

Next, the thin film scattering step is to detect an intensity of a signal scattered by the special component contained in the base layer by irradiating the x-ray to the thin film layer formed on the base layer of the reference sample. That is, although the base layer irradiation step has detected an intensity of a signal relative to a reference sample with no thin film layer, the thin film layer irradiation step is to detect an intensity of a signal of a reference sample with a thin film layer, and the intensities of two signals are compared to determine an intensity of a signal changed (decreased) by the thin film layer.

Figure 1:
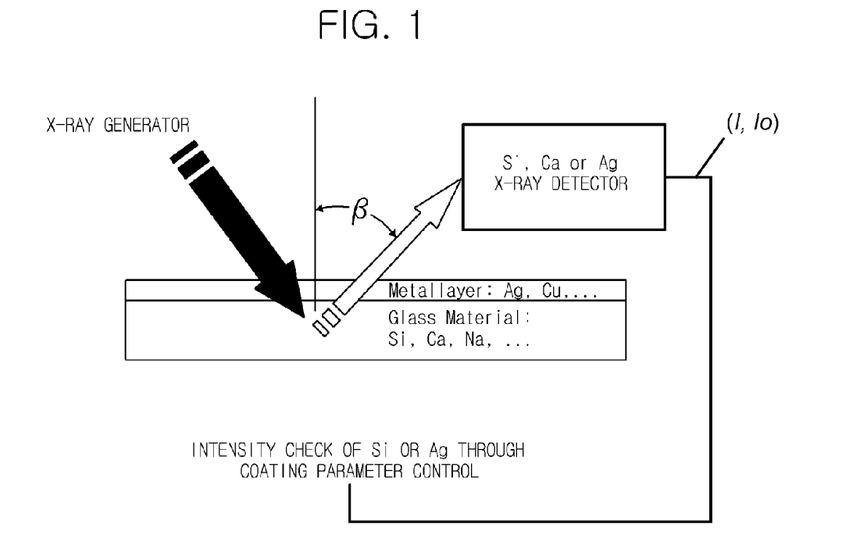
FIG. 1 is a conceptual view illustrating a state where an x-ray is scattered on a base layer according to an exemplary embodiment of the present disclosure.

FIG. 1 is a conceptual view illustrating a state where an x-ray is scattered on a base layer according to an exemplary embodiment of the present disclosure, wherein a case x-ray is irradiated on the base layer formed with the thin film layer, an intensity (I) of signal scattered by the thin film layer is changed in comparison with the base layer formed with no thin film layer ($I_o$). That is, the number of emitted electrons of the scattered x-ray may be decreased by the thin film layer, signal of x-ray may be decreased, or wavelength may be changed, which is differently exhibited in response to thickness of the thin film layer, and which is proportionate to the thickness of the thin film layer.

Hence, the calibration curve determination step is to determine a calibration curve by comparing the difference of intensities of signals respectively detected by the base layer irradiation step and the thin film layer irradiation step with an actual thickness of the thin film layer. That is, in a reference sample having a base layer, and a reference sample having a base layer formed with a thin film layer, a calibration curve is determined using a difference of intensities of signals as a base by a special component contained in the base layer changed or decreased in response to an actual thickness of the thin film layer.

To this end, there is a need of learning in advance the actual thickness of the thin film layer, such that the method according to the present disclosure may further comprise measuring a thickness of thin film layer formed on the base layer of the reference sample using an electron microscope.

Figure 2:
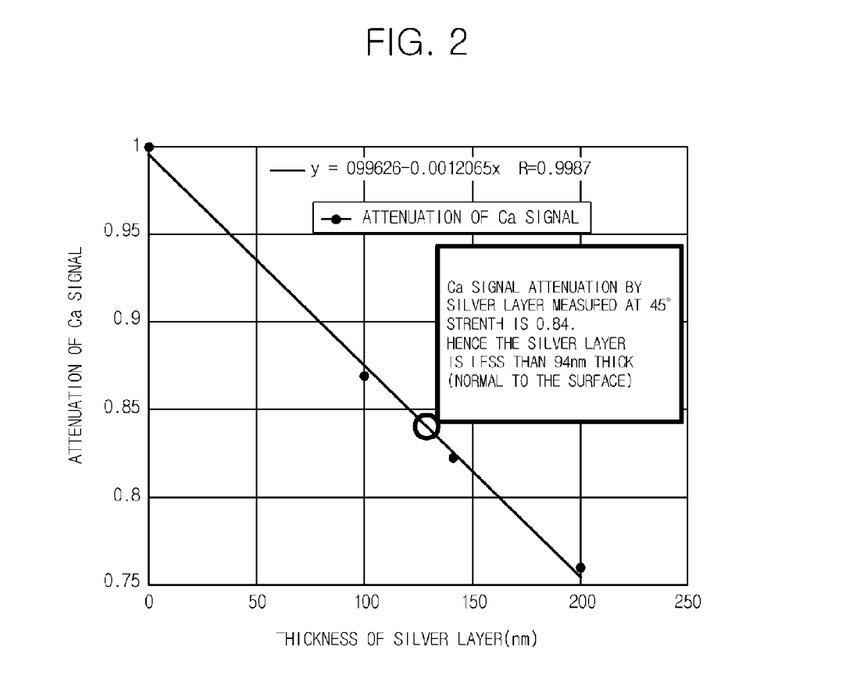
FIG. 2 is a graph illustrating an example of a calibration curve according to the present disclosure.
Figure 3:
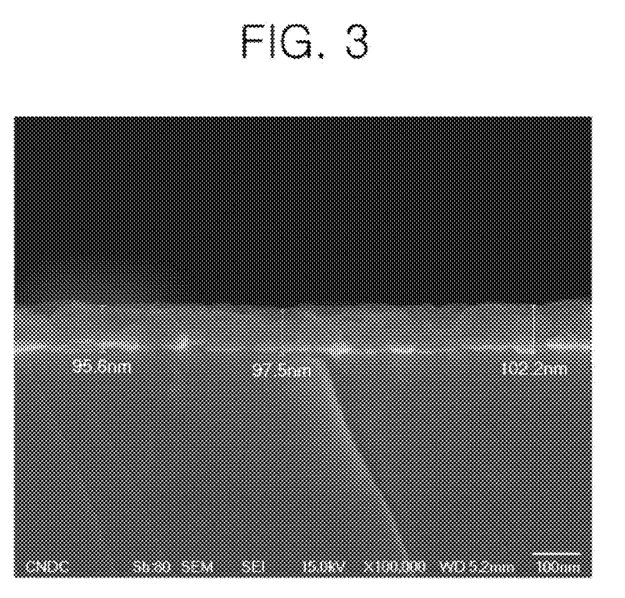
FIGS. 3 to 14 are, respectively, analytical photographs photographed by an FEM SEM of samples 1~12 having a silver layer according to an exemplary embodiment of the present disclosure.
Figure 4:
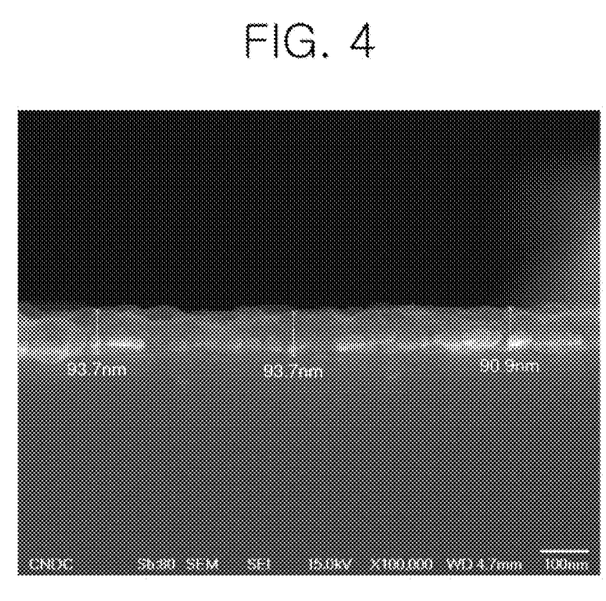
Figure 5:
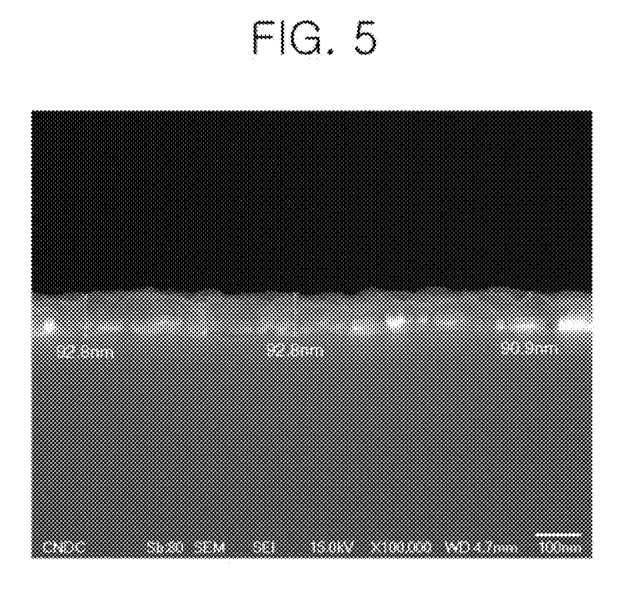
Figure 6:
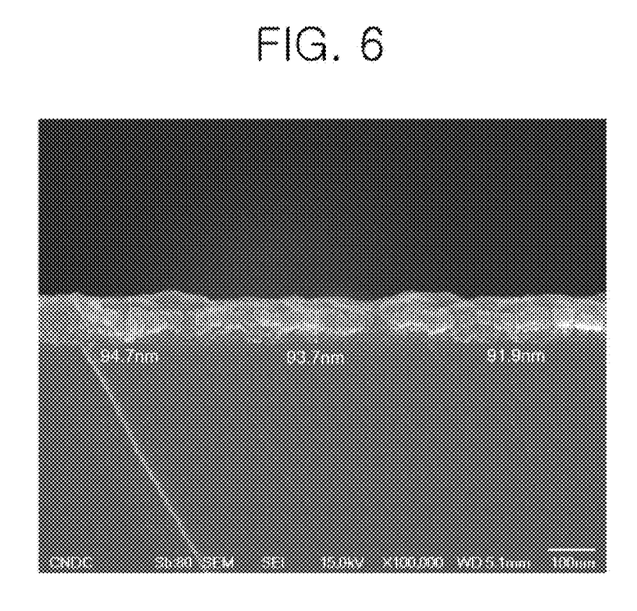
Figure 7:
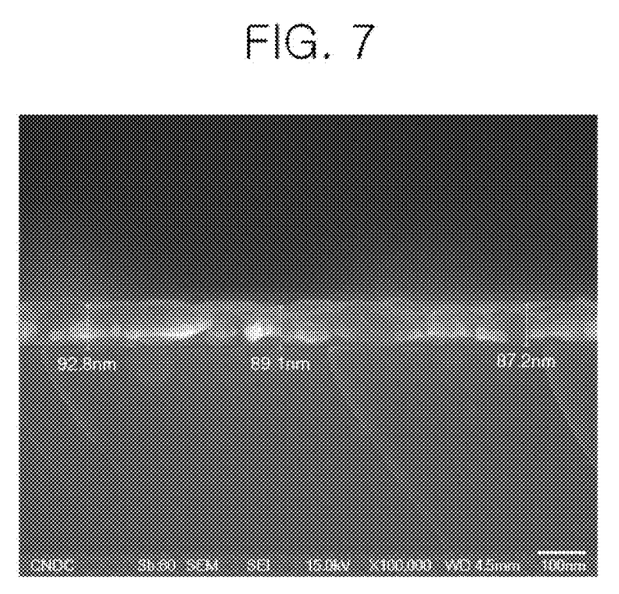
Figure 8:
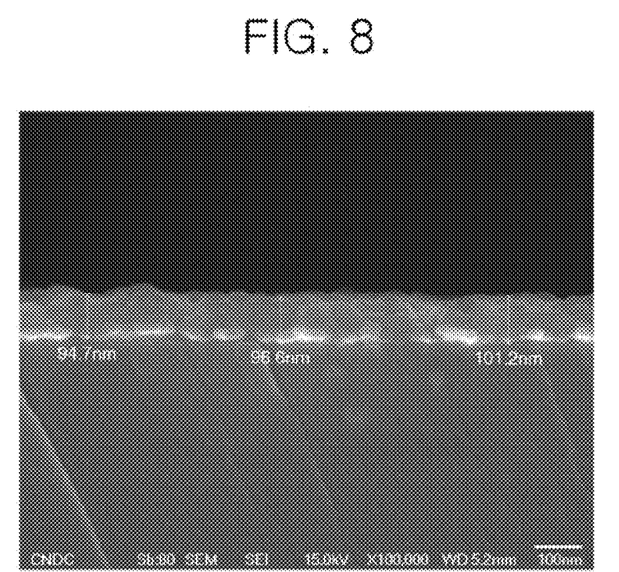
Figure 9:
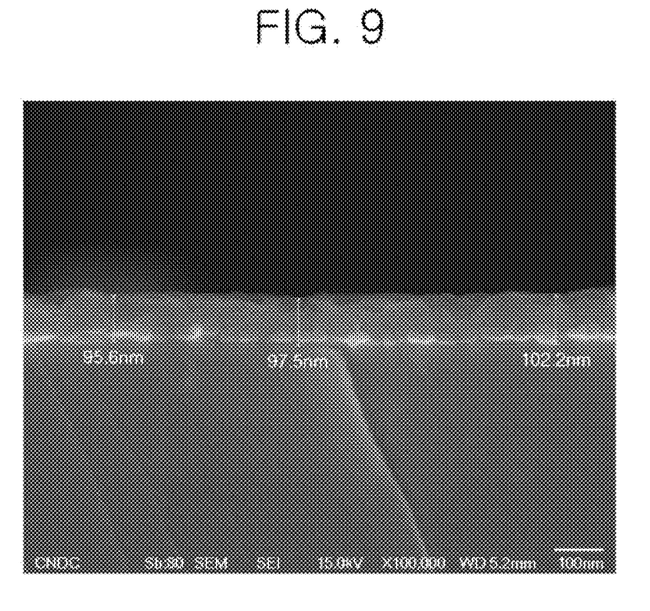
Figure 10:
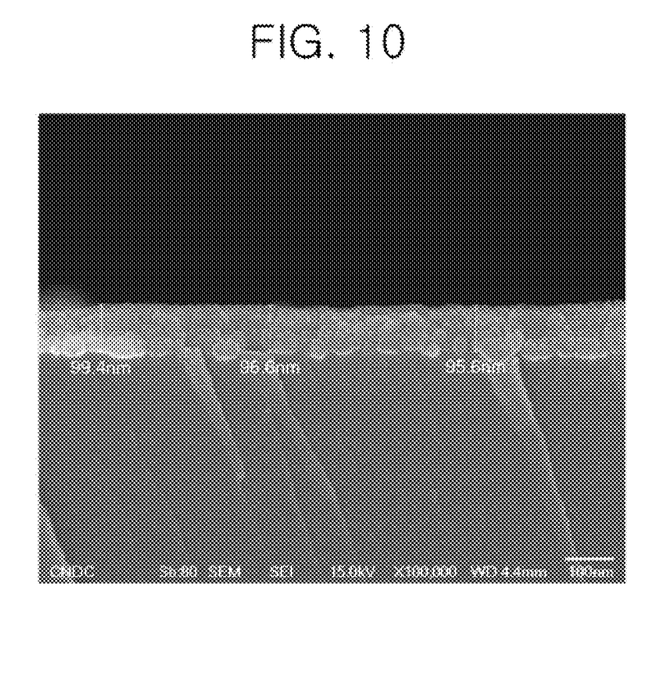
Figure 11:
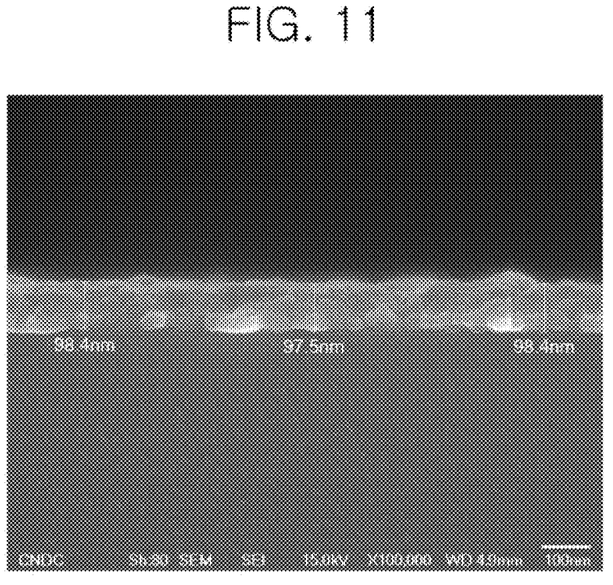
Figure 12:
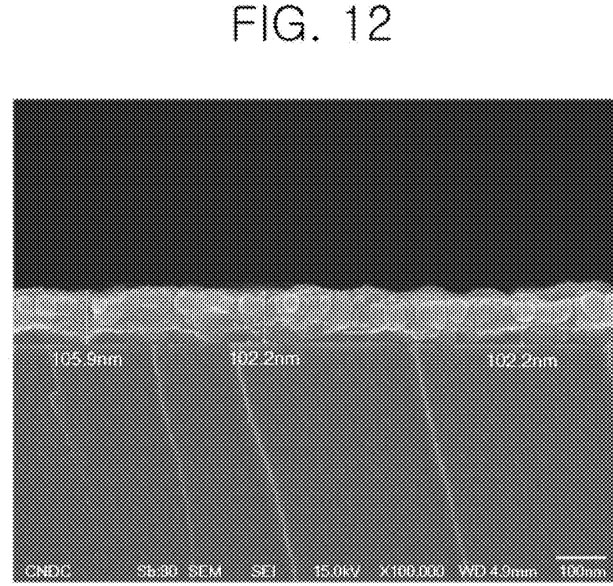
Figure 13:
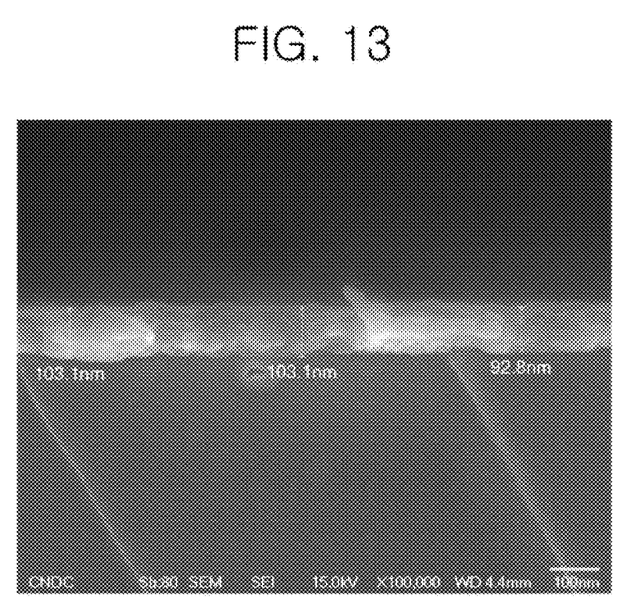
Figure 14:
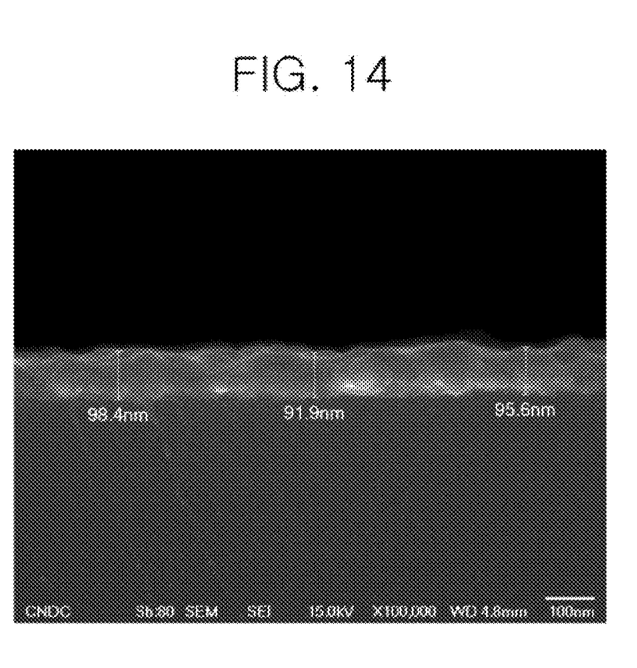

FIG. 2 is a graph illustrating an example of a calibration curve according to the present disclosure, where, y axis defines a difference of intensities of signals respectively detected in the base layer irradiation step and the thin film layer irradiation step, x axis defines a thickness of thin film layer measured by SEM in response to the difference of intensities, and where, using a reference sample formed of a silver layer on a glass substrate as an object, the intensity of signal scattered by calcium elements included in the glass substrate is based.

The determination of calibration curve may be determined by an x-ray mass attenuation coefficient: $\mu/\rho$) as shown in the following Equation 1. That is, a ratio of intensity of signal of a thin film layer relative to the base layer of the reference sample or the target sample is proportionate to density of thin film layer, in reverse proportionate to the thickness, and the attenuation coefficient ($\mu$) of the thin film layer may be differently set by the types of thin film layers, ingredients, thickness and incident angle of the x-ray.

$$I/I_o = \exp[-(\mu/\rho)X] \quad \text{Equation 1}$$

I: intensity of returning signal relative to thin film layer
Io: intensity of returning signal relative to base layer
$\mu$: attenuation coefficient of thin film layer
$\rho$: density of thin film layer
X: thickness of thin film layer The abovementioned Equation 1 may be $\mu/\rho = X^{-1} \ln(I_o/I)$, and if the thin film layer is a multilayered structure [t], thickness of multilayered structure may be calculated from I.e. $X = \rho t$.

Furthermore, the calibration curve determination step may include correction by comparing a difference between intensities of signals with an actual thickness of thin film layer in order to enhance the accuracy.

Successively, the target sample irradiation step may include irradiating x-ray on a thin film layer formed on the base layer of the target sample to detect an intensity of a signal scattered by the special component contained in the base layer.

Although the abovementioned step has determined calibration curve using the reference sample an object, the target sample irradiation step is to detect an intensity of a returning signal of x-ray relative to a target sample that is an object of analysis. The target sample is not destructed, but x-ray is directly irradiated on a base layer containing the thin film layer, where the base layer and the thin film layer of the target sample are preferably same as or similar to those of the reference sample for comparison with the reference sample.

Furthermore, the thin film layer determining step determines the thickness of the thin film layer of the target sample by comparing a difference of intensities of signals respectively detected in the base layer irradiation step and the target sample irradiation step. That is, a difference of intensities of signals respectively detected in the base layer irradiation step relative to the reference sample and in the target sample irradiation step is calculated without destructing the target sample, which is then compared with the calibration curve to indirectly determine the thickness of thin film layer of the target sample.

In another general aspect of the present disclosure, there is provided an apparatus for measuring thickness of thin film using x-ray, where the apparatus, in particular, comprises an x-ray generator, a detector, and a controller.

The x-ray generator irradiates x-ray to a base layer or a thin film layer of a reference sample or a target sample. The x-ray generator includes an x-ray tube (not shown), a high voltage generator (not shown) and various security circuits (not shown). The x-ray tube, which is a thermal electron 2-pole vacuum tube, accelerates thermal electrons from a cathode (generally tungsten filament) and makes the accelerated thermal electrons collide with an anticathode to generate x-ray. Flow of electrons toward the anticathode is generally broadly dispersed to apply an appropriate magnetic field to a Wehnelt cylinder, whereby flow of electrons is prevented from being diverged. In order to generate the x-ray, the high-voltage generator generates a high negative voltage and supplies the high negative voltage to the x-ray tube. The security circuit warns the x-ray generator occurrence of high load, high voltage and low voltage at the x-ray generator during generation of x-ray.

The detector serves to detect intensity of a signal scattered from the reference sample or the target sample. The detector receives the x-ray reflected from the reference sample and the target sample to detect a level of intensity of reflected x-ray. That is, the detector measures an intensity value of x-ray reflected from the sample substrate. The detector may be disposed in a pair, and an example of the detector may be a PC (Proportional Counter) and a SC (Scintillation Counter).

The present disclosure may further include an analysis splitter disposed on a path of x-ray reflected from the sample substrate to filter on a special x-ray having a particular wavelength among the x-rays reflected from the sample substrate. At this time, the x-ray reflected from the sample substrate corresponds to an x-ray that is generated when electrons move from a high energy level to a low energy level while being irradiated to the sample substrate.

The controller determines a calibration curve by comparing a difference of contents of special components included in a base layer of a reference sample respectively having the base layer and a base layer formed with a thin film layer, with the thickness of the thin film layer, and determines the thickness of thin film layer of a target sample by comparing a difference of contents of special components included in a base layer of a target sample having a base layer formed with a thin film layer and a reference sample having the base layer, with the calibration curve.

The present disclosure can accurately measure a thin nanometer-level film thickness using x-ray without destructing a target sample. Furthermore, the present disclosure can provide a method and apparatus for measuring thickness of thin film using x-ray configured to easily and simply measure the thickness of thin film layer using a test subject having a thin film layer formed on a substrate or a base layer as an object, and configured to be used in a unit process and a continuous process as well.

The present disclosure may be well understood by the following exemplary embodiments, which are provided by way of example only, not by way of limitations.

First Exemplary Embodiment: Measurement of Silver Layer Thickness

The present inventor prepared, on a glass substrate, samples #1~12 each having a silver layer, measured a thickness of the silver layer using X-ray and FEM SEM according to the present disclosure, and obtained the following results as shown in Table 1, and FIGS. 3 to 14. FIGS. 3 to 14 are, respectively, analytical photographs photographed by an FEM SEM of samples 1~12 having a silver layer according to an exemplary embodiment of the present disclosure;

TABLE 1

| | Sample number items | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| analytical result by FEM SEM [nm] | 98 | 94 | 93 | 94 | 90 | 97 | 98 | 97 | 98 | 102 | 103 | 98 |
| analytical result by X-ray [nm] | 95 | 93 | 91 | 93 | 91 | 95 | 98 | 96 | 99 | 102 | 102 | 97 |

As evidenced in Table 1, it can be noted that there is a substantial or near similarity between the analytical result by FEM SEM and the analytical result by X-ray according to the present disclosure.

Figure 15:
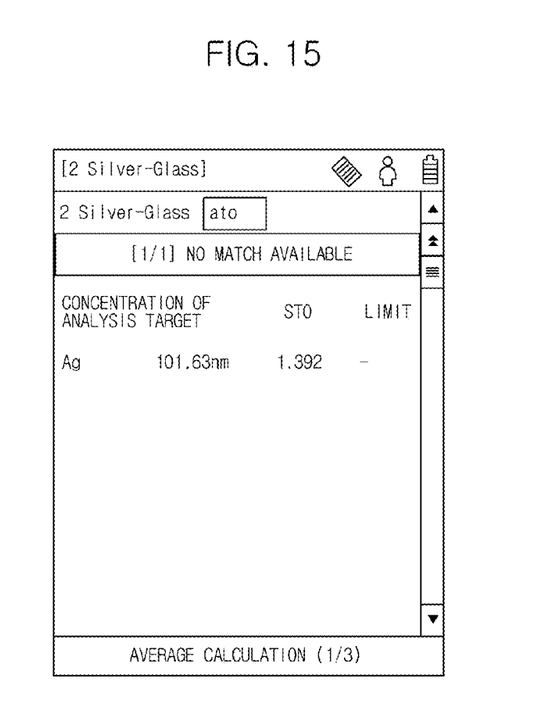
FIG. 15 is a display screen illustrating a thickness measurement result of a sample #10 using x-ray according to an exemplary embodiment of the present disclosure.

FIG. 15 is a display screen illustrating a thickness measurement result of a sample #10 using x-ray according to an exemplary embodiment of the present disclosure.

Second Exemplary Embodiment: Measurement of Copper Layer Thickness

Figure 16:
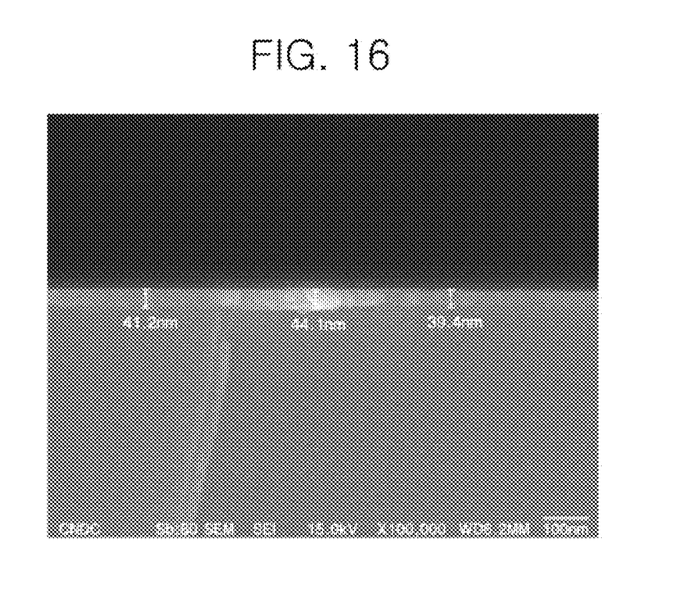
FIGS. 16 and 17 are, respectively, analytical photographs photographed by an FEM SEM of samples 13~14 having a copper layer according to an exemplary embodiment of the present disclosure.
Figure 17:
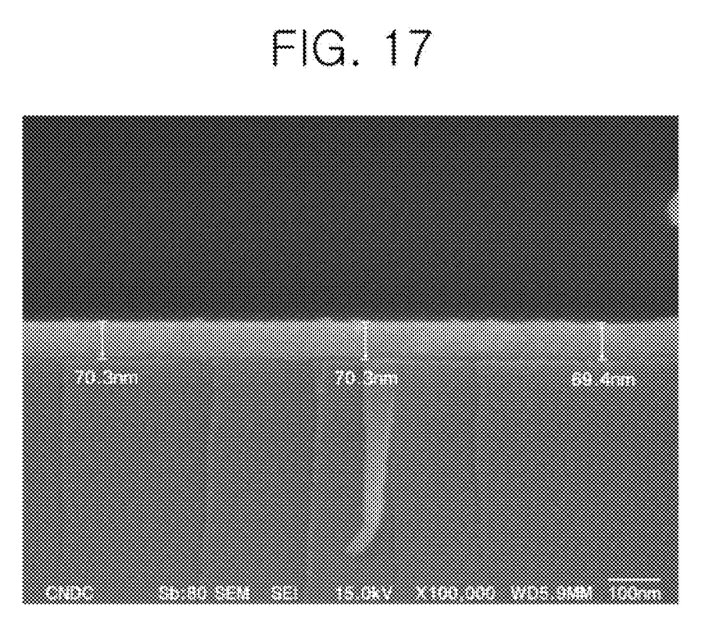

The present inventor prepared, on a glass substrate, samples #13 and 14 having a copper layer, measured a thickness of the copper layer using X-ray and FEM SEM according to the present disclosure, and obtained the following results as shown in Table 2, and FIGS. 16 and 17.

FIGS. 16 and 17 are, respectively, analytical photographs photographed by an FEM SEM of sample #13~14 having a copper layer according to an exemplary embodiment of the present disclosure.

TABLE 2

| Sample number items | 13 | 14 |
|---|---|---|
| analytical result by FEM SEM [nm] | 44 | 70 |
| analytical result by X-ray [nm] | 43 | 69 |

As evidenced in Table 2, it can be noted that there is a substantial or near similarity between the analytical result by FEM SEM and the analytical result by X-ray according to the present disclosure.

Third Exemplary Embodiment: Measurement of Silver Layer Thickness and Copper Layer Thickness The present inventor prepared, on a glass substrate, samples #15 and 16 having a copper layer and a silver layer, measured a thickness of the copper layer using X-ray and STEM (scanning transmission electron microscope) methods according to the present disclosure.

1. A transmission detector (STEM) was mounted on the STEM to analyze a specimen manufactured in a thin film layer (Lamella) shape, where the analytical data shape is same as that of the above FE SEM method, but a pre-process method of specimen is different.
2. When preparing the specimen, the FIB (Focused Ion Beam) method was used in case of FEM SEM, and the FIB was adjusted to analyze the formation of cross-section of the specimen, and a specimen of Lamella shape was manufactured, the manufacturing method of which is same as that of transmission electron microscope.
3. The specimen is lamella shape is horizontally fixed on the electron microscope, and irradiated with electron beam to obtain an image, where a thickness of coated thin film was measured using an accurately-calibrated software scale. The results of which are shown in the following Table 3 and FIGS. 18 and 19.

Figure 18:
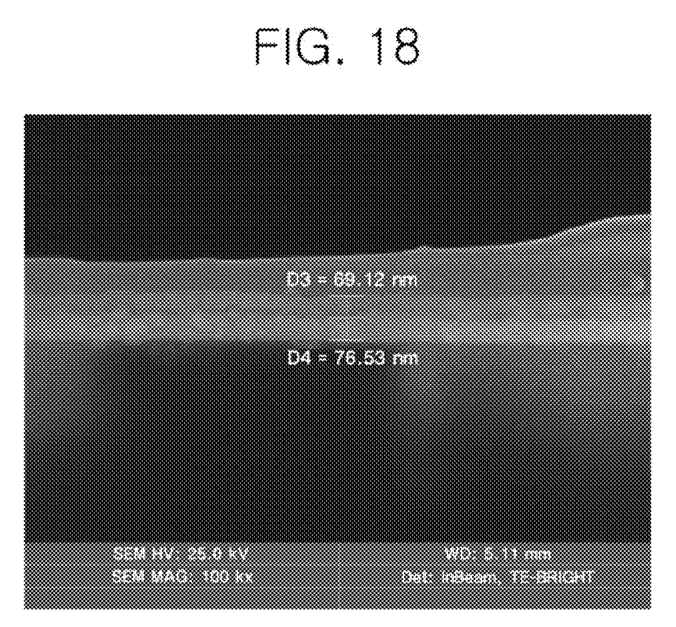
FIGS. 18 and 19 are, respectively, analytical photographs photographed by an FEM SEM of samples 15~16 having a silver layer and a copper layer according to an exemplary embodiment of the present disclosure.
Figure 19:
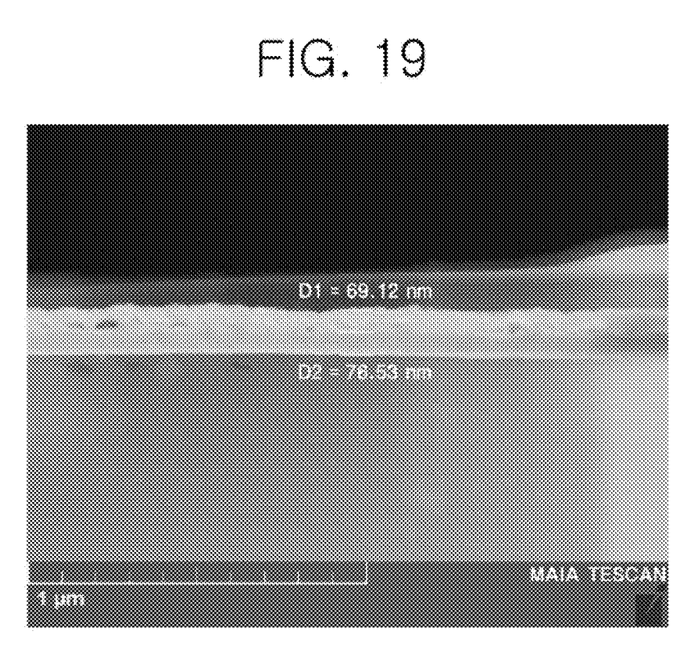

FIGS. 18 and 19 are, respectively, analytical photographs photographed by an FEM SEM of samples #15~16 having a silver layer and a copper layer according to an exemplary embodiment of the present disclosure.

TABLE 3

| Sample number items | | 15 | 16 |
|---|---|---|---|
| analytical result by STEM [nm] | silver | 76 | 76 |
| | copper | 69 | 69 |
| analytical result by X-ray [nm] | silver | 75 | 76 |
| | copper | 68 | 68 |

As evidenced in Table 3, it can be noted that there is a substantial or near similarity between the analytical result by FEM SEM and the analytical result by X-ray according to the present disclosure.

Fourth Exemplary Embodiment: Measurement of Thickness of Metal Layer

The present inventor prepared, on a glass substrate, silver, copper, nickel and iron samples each with a thickness of 500 nm, and each thickness was measured using FEM SEM. Each thickness of metal layers was measured using the x-ray method according to the present disclosure, the results of which are provided in the following Table 4.

TABLE 4

| Metals | silver | copper | nickel | iron |
|---|---|---|---|---|
| analytical result by X-ray | Thickness immeasurable | Thickness immeasurable | Thickness immeasurable | Thickness immeasurable |

As evidenced from the Table 4, it can be noted that the thickness of metal layer having approximately 500 nm-level or more cannot be measured using the x-ray method according to the present disclosure.

Although the present disclosure has been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of subject combination arrangement within the scope of the disclosure, the drawings and the appended claims. In addition to variations and modifications in the component parts and/or arrangements, alternative uses will also be apparent to those skilled in the art.

What is claimed is:

1. A method for measuring thickness of thin film using x-ray, the method comprising:
    detecting an intensity of a signal scattered by a special component included in a reference base layer of a first reference sample by irradiating x-ray to the reference base layer of the first reference sample;
    forming a reference thin film layer on a base layer of a second reference sample;
    detecting an intensity of a signal scattered by the special component included in the base layer of the second reference sample by irradiating x-ray to the reference thin film layer formed on the base layer of the second reference sample;
    measuring an actual thickness of the reference thin film layer formed on the base layer of the second reference sample using an electron microscope;
    determining a calibration line as a ratio of the intensity of the signal from the reference thin film layer relative to the intensity of the signal from the reference base layer of the first reference sample; wherein a y axis of the calibration line represents a ratio of intensities of signals respectively detected in the reference base layer irradiation step and the reference thin film layer irradiation step, and an x axis of the calibration line represents thickness of thin film layers measured by the electron microscope;
    detecting an intensity of a signal scattered by the special component included in a target base layer by irradiating x-ray to a target thin film layer formed on the base layer of a target sample; and
    determining a thickness of the target thin film layer of the target sample by calculating a target sample ratio between intensities of signals respectively detected from the target sample irradiation step and the reference base layer irradiation step, where the thickness of the target thin film layer of the target sample is the thickness corresponding to the target sample ratio along the calibration line;
    wherein the thickness of the target thin film layer is from 50 nm to 300 nm,
    wherein the reference thin film layer and the target thin film layer are formed with the same material, and
    wherein the reference base layer and the target base layer are formed with the same material.

2. The method of claim 1, wherein the reference base layer and the target base layer are glass substrates.

3. The method of claim 1, wherein the reference thin film layer and the target thin film layer are metal layers selected from a group consisting of silver, copper, nickel, manganese, chrome, iron, and gold.

4. The method of claim 1, wherein the special component is selected from a group consisting of C, H, O, Ca, Na, Si, and Ag.

5. The method of claim 1, wherein the special component is C, H, O, Ca, Na, Si, or Ag.

6. The method of claim 1, wherein the special component is not present in the reference thin film layer and the target thin film layer but present only in the reference base layer and the target base layer.

7. The method of claim 5, wherein the special component is not present in the reference thin film layer and the target thin film layer but present only in the reference base layer and the target base layer.

8. The method of claim 1, wherein the x-ray is irradiated by a portable XRF (X-ray Fluorescence) spectrometer.

9. The method of claim 1, wherein the calibration line is determined by the following Equation:

$$I/Io = \exp[-(\mu/\rho)X]$$

I: scattered signal intensity coming from the base layer being absorbed by the reference thin film layer
Io: scattered signal intensity coming from the reference base layer
$\mu$: attenuation coefficient of the reference thin film layer
$\rho$: density of the reference thin film layer
X: thickness of the reference thin film layer.

10. The method of claim 3, wherein the calibration line is determined by the following Equation:

$$I/Io = \exp[-(\mu/\rho)X]$$

I: scattered signal intensity coming from the base layer being absorbed by the reference thin film layer
Io: scattered signal intensity coming from the reference base layer
$\mu$: attenuation coefficient of the reference thin film layer
$\rho$: density of the reference thin film layer
X: thickness of the reference thin film layer.

11. The method of claim 5 wherein the calibration line is determined by the following Equation:

$$I/Io = \exp[-(\mu/\rho)X]$$

I: scattered signal intensity coming from the base layer being absorbed by the reference thin film layer
Io: scattered signal intensity coming from the reference base layer
$\mu$: attenuation coefficient of the reference thin film layer
$\rho$: density of the reference thin film layer
X: thickness of the reference thin film layer.

12. The method of claim 6, wherein the calibration line is determined by the following Equation:

$$I/Io = \exp[-(\mu/\rho)X]$$

I: scattered signal intensity coming from the base layer being absorbed by the reference thin film layer Io: scattered signal intensity coming from the reference base layer μ: attenuation coefficient of the reference thin film layer ρ: density of the reference thin film layer X: thickness of the reference thin film layer.

13. The method of claim 8, wherein the calibration line is determined by the following Equation:

$$I/Io=\exp[-(\mu/\rho)X]$$

I: scattered signal intensity coming from the base layer being absorbed
by the reference thin film layer Io: scattered signal intensity coming from the reference base layer μ: attenuation coefficient of the reference thin film layer ρ: density of the reference thin film layer X: thickness of the reference thin film layer.

14. An apparatus for measuring thickness of thin film using x-ray, the apparatus comprising:

an x-ray generator irradiating x-ray to a reference base layer of a first reference sample, a reference thin film layer of a second reference sample, a base layer of a target sample and a target thin film layer of the target sample, wherein the reference thin film layer is formed on a base layer of the second reference sample;

a detector detecting intensity of a signal scattered from the first reference sample, the second reference sample and the target sample;

an electron microscope measuring an actual thickness of the reference thin film layer formed on the base layer of the second reference sample; and a controller determining a calibration line as a ratio of the intensity of the signal from the reference thin film layer formed on the base layer of the second reference sample relative to the intensity of the signal from the reference base layer of the first reference sample, wherein a y axis of the calibration line represents a ratio of intensities of signals respectively detected in the first base layer irradiation step and the first thin film layer irradiation step, and an x axis of the calibration line represents the thickness of thin film layers, and determining a thickness of the target thin film layer of the target sample by calculating a target sample ratio between intensities of signals scattered by the special component included in the reference base layer of the first reference sample and the target sample where the thickness of the target thin film layer of the target sample is the thickness corresponding to the target sample ratio along the calibration line, wherein the thickness of the target thin film layer is from 50 nm to 300 nm, wherein the reference thin film layer and the target thin film layer are formed with the same material, wherein the base layer of the first reference sample, the base layer of the second reference sample, and the target base layer are formed with the same material.

15. The apparatus of claim 14, wherein the special component is C, H, O, Ca, Na, Si, or Ag.

* * * * *